United States Patent
Rochette

(10) Patent No.: US 9,731,068 B2
(45) Date of Patent: Aug. 15, 2017

(54) DRIVE HEAD FOR A SYRINGE PUMP

(75) Inventor: Francois Rochette, Apprieu (FR)

(73) Assignee: Fresenius Vial SAS, Brézins (FR)

( * ) Notice: Subject to any disclaimer, the term of this patent is extended or adjusted under 35 U.S.C. 154(b) by 841 days.

(21) Appl. No.: 13/400,978

(22) Filed: Feb. 21, 2012

(65) Prior Publication Data

US 2012/0234099 A1    Sep. 20, 2012

Related U.S. Application Data

(60) Provisional application No. 61/453,143, filed on Mar. 16, 2011.

(30) Foreign Application Priority Data

Mar. 16, 2011   (EP) ..................................... 11158391

(51) Int. Cl.
| | | |
|---|---|---|
| *G01L 7/00* | (2006.01) | |
| *A61M 5/145* | (2006.01) | |
| *A61M 5/168* | (2006.01) | |

(52) U.S. Cl.
CPC ...... *A61M 5/1458* (2013.01); *A61M 5/14566* (2013.01); *A61M 5/16854* (2013.01); *A61M 2205/332* (2013.01)

(58) Field of Classification Search
CPC ...... A61M 2205/3331; A61M 5/16854; A61M 5/1458; A61M 5/283; A61M 2005/3245; A61M 2005/3252; A61M 5/14546; A61M 2005/14573; A61M 5/14566
USPC ................................. 604/228–229
See application file for complete search history.

(56) References Cited

U.S. PATENT DOCUMENTS

| | | | | |
|---|---|---|---|---|
| 5,254,096 A | * | 10/1993 | Rondelet | A61M 5/1456 417/63 |
| 5,261,882 A | * | 11/1993 | Sealfon | A61M 5/1454 128/DIG. 12 |
| 6,368,307 B1 | * | 4/2002 | Ziemba | A61M 5/14546 604/131 |
| 6,428,509 B1 | * | 8/2002 | Fielder | A61M 5/1456 604/131 |
| 7,666,169 B2 | * | 2/2010 | Cowan et al. | 604/228 |

(Continued)

FOREIGN PATENT DOCUMENTS

| | | |
|---|---|---|
| EP | 0229450 | 7/1987 |
| EP | 0314880 | 5/1989 |

(Continued)

*Primary Examiner* — Bhisma Mehta
*Assistant Examiner* — William Frehe
(74) *Attorney, Agent, or Firm* — Occhiuti & Rohlicek LLP

(57) ABSTRACT

The invention concerns a connection device for connecting a first reservoir with a second reservoir, having
a first section (11) for arranging the first reservoir (5) closed with a seal (51);
a second section (12) for arranging the second reservoir; and
a piercing element (2) which penetrates with a piercing end (21) the seal (51) of the first reservoir (5) when the first reservoir (5) is arranged at the first section (11).
According to the invention, the piercing element (2) can be moved from a first position into a second position, wherein it blocks in the first position a flow connection between the first and the second section (11, 12), while in the second position it allows for a flow connection between the first and the second section (11, 12).

14 Claims, 12 Drawing Sheets

(56) References Cited

U.S. PATENT DOCUMENTS

2003/0229311 A1* 12/2003 G. Morris ........... A61M 5/1456
604/151
2008/0262440 A1* 10/2008 Rochette ............. A61M 5/1458
604/228
2010/0214110 A1   8/2010 Wang et al.

FOREIGN PATENT DOCUMENTS

EP     0916353    5/1999
WO    01/08726    2/2001

* cited by examiner

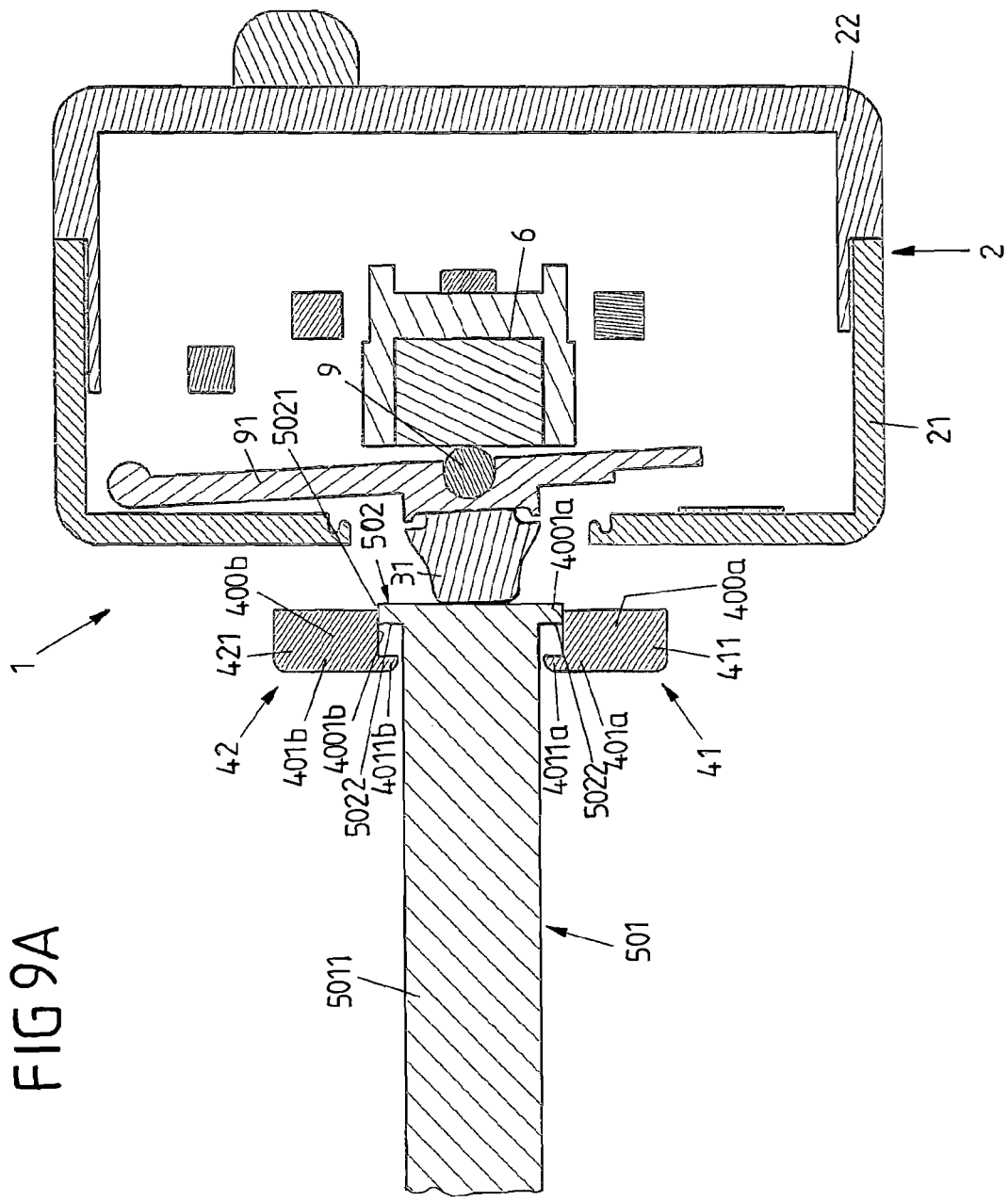

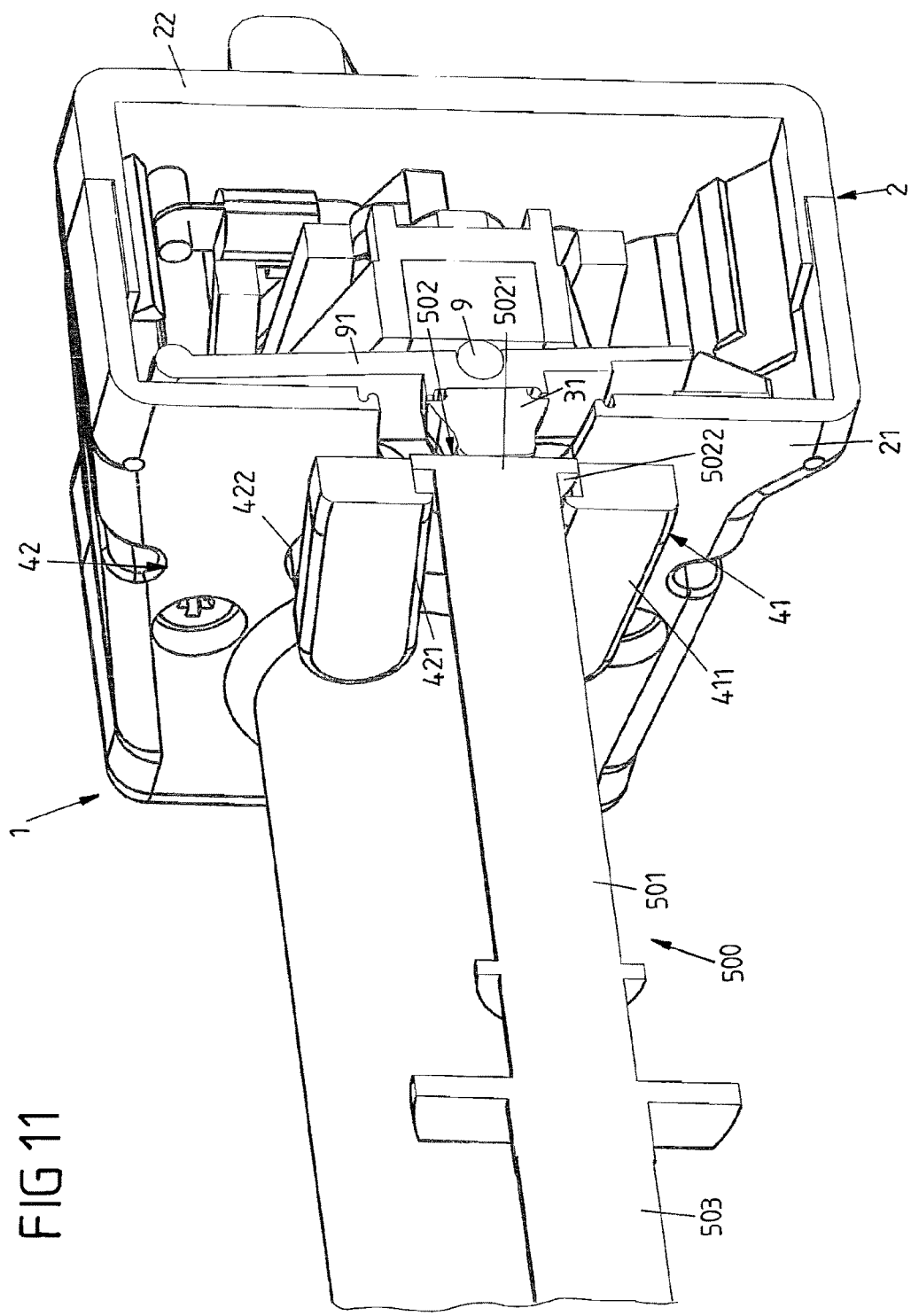

DRIVE HEAD FOR A SYRINGE PUMP

CROSS REFERENCE TO RELATED APPLICATIONS

This application claims priority to European Application No. 11 158 391.0 and U.S. Provisional Application No. 61/453,143, both filed on Mar. 16, 2011. The contents of the aforementioned applications are incorporated herein by reference.

The invention relates to a drive head for a syringe pump according to the preamble of claim 1.

Syringe pumps for emptying a syringe are known from the prior art. For example, syringe pumps are used in the medical field in order to infuse a liquid contained in a syringe into a human body. The known syringe pumps typically comprise a drive head connected to a drive mechanism configured to generate a linear movement of the drive head such that a plunger of the syringe will be moved within the syringe barrel by the drive head. It is also known to arrange a pressure sensor at the drive head in order to be able to measure an inner pressure of the syringe during operation of the syringe pump. A syringe pump including such a drive head is disclosed, for example, in EP 0 916 353 A1.

It is an object of the invention to provide a drive head for a syringe pump that allows a measurement of the inner pressure within the syringe as accurate as possible.

This problem is solved by the drive head according to claim 1. Embodiments of the inventions are defined in the dependent claims.

According to the invention, a drive head for a syringe pump is provided, comprising
  a contact portion configured to bear against a plunger of a syringe in order to move the plunger relative to a barrel of the syringe;
  at least one holding element for holding a flange of the syringe plunger in order to prevent a siphon movement of the plunger away from the contact portion;
  a pressure sensor for determining an inner pressure in the syringe, the pressure sensor being arranged at a pressure sensor support of the drive head; and
  a housing in which the pressure sensor support and the pressure sensor are arranged, wherein
  the holding element is mounted via the pressure sensor support.

The pressure sensor allows to determine the pressure inside the syringe by determining the force that is exerted by the syringe plunger on the contact portion of the drive head. This force F depends on the inner pressure p of the syringe and the cross section S of the plunger according to $F=p \cdot S$ such that the inner pressure can be determined if F is known.

In order to determine the inner pressure in the syringe as precisely as possible it is thus necessary to be able to carry out an accurate measurement of the force F applied by the syringe plunger to the contact portion. In order to avoid that a parasitic force is applied to the contact portion of the drive head via the holding element, which in operation of the drive head bears against the syringe plunger, the holding element is mounted via the pressure sensor support and, for example, not via the housing of the drive head. The holding element may be an anti-siphon arm as further explained below.

Due to the mounting of the holding element via the pressure sensor support parasitic forces transferred via the holding element to the contact portion and thus to the pressure sensor will be reduced or avoided. Also, it is possible to separate a parasitic force distribution induced via the holding elements from the actual force applied to the bearing section. For example, an electrical signal generated by the pressure sensor can be analysed and a force contribution introduced via the holding element can be identified.

The housing of the drive head may comprise an opening through which the holding element extends with a distance to an inner edge of the opening, i.e. without resting on the edge of the opening such that the holding element can be considered to be mounted in a floating manner. The floatingly mounted holding element prevents, for example, that a deformation of the drive head housing is transferred via the holding element and contact portion to the pressure sensor such that distortions of the pressure sensor signal are avoided as much as possible.

Further, the pressure sensor support may be arranged on a side of the contact portion that faces away from the syringe when the drive head is in operation. For example, the pressure sensor support is arranged in a distance from the contact portion, i.e. the pressure sensor support is not in direct contact with the contact portion. For example, the pressure sensor support comprises a block formed by a metal or plastic, the block being arranged within the housing of the drive head.

Although located in a distance to the contact portion, the pressure sensor support may still be arranged in such a way that a force exerted by the syringe plunger to the contact portion is transferred to the pressure sensor through the pressure sensor support. For example, the pressure sensor comprises a strain gauge arranged at a surface of the pressure sensor support that faces away from the contact portion. In that example, the force applied by the syringe plunger to the contact portion is transferred (directly or indirectly) to the pressure sensor support and via the pressure sensor support to the strain gauge.

For example, the pressure sensor support comprises a first part carrying the pressure sensor and a second part via which the holding element is mounted. The second part may have an opening through which a part (e.g. a shaft as set forth below) of the holding element at least partially extends. The first and the second part may be integrally connected to one another. However, in another example of the invention, the second part is connected to the first part via connecting means (e.g. in a form-closed or force-closed manner).

According to another embodiment of the invention, the first part of the pressure sensor device comprises a front side facing towards the contact portion and a back side facing away from the bearing section, the pressure sensor being connected to the back side. For example, the front side runs parallel to the back side.

The pressure sensor support may be designed in such a way that if the front side is deformed under the impact of a force applied to the front side (via the contact portion) the back side is deformed in similar way such that a portion of the front and the back side remain parallel to a plane along which the front and the back side extended before the deformation. Thus, during operation of the drive head the front and the back side of the pressure sensor support remain parallel such that it can be avoided that the second part of the sensor support inclines when the syringe flange presses against the contact portion. Thus, it can be avoided that holding element, which is mounted via the second part, is inclined relative to the syringe plunger if a force is applied to the pressure sensor support via the bearing section.

For example, the design of the pressure sensor support may provide a through opening running essentially parallel to the back side of the pressure sensor support. According to an example, the through opening has a cross section that is formed by two partially overlapping circles whose centres are positioned on an imaginary line running parallel to the front and the back side of the pressure sensor support. Thus, the pressure sensor support tends to bend in the region of the trough opening and not outside the through opening, i.e. lateral to the through opening (viewed in a direction perpendicular to the direction of movement of the drive head). According to another embodiment, the pressure sensor is arranged on the back side of the pressure sensor support in the region of the through opening, i.e. behind the through opening (viewed in a direction parallel to the direction of movement of the drive head).

Further, the drive head may comprise a pressure transmitting element arranged in a carrier, wherein is side of the contact portion is pushed towards the carrier if the syringe plunger applies a force on the contact portion such that the carrier and thus the pressure transmitting element is pushed against the pressure sensor support. For example, the pressure transmitting element is a cylindrical, conical or spherical element, e.g. formed by metal or plastic.

According to another embodiment of the invention, the contact portion is arranged in a portion of the housing. For example, the contact portion is a section of the housing (e.g. a housing sidewall), i.e. integrally formed with the housing.

In another example, the contact portion comprises a contact element that is arranged in such a manner that the plunger of the syringe, when the syringe pump drive head is operated, is pushed by the contact portion, i.e. the contact element receives the force applied by the syringe plunger and transfers the force (directly or indirectly) towards the pressure sensor support. In particular, the contact portion is mounted to the drive head housing via a flexible element (formed by a resilient material), e.g. a membrane.

For example, the contact element protrudes from an outer side of the drive head housing towards the syringe plunger, i.e. it is formed as a "finger" receiving the plunger force applied by the syringe plunger and conveying the force to the pressure sensor support. For example, the contact element is pushed against the carrier comprising the pressure transmitting element as mentioned above.

The protruding contact element may be surrounded by a flexible element in the form of a membrane which is connected to the contact element via a first portion (e.g. via a bond connection) and which comprises a second portion that is connected to the housing (e.g. also via bonding).

Moreover, the holding element may be rotatably mounted at the pressure sensor support. For example, the holding element comprises a shaft that at least partially reaches through the pressure sensor support such that the pressure sensor support allows a rotational movement of the shaft and thus the holding element. As mentioned above, the holding element could be an anti-siphon arm comprising a gripping element for holding (e.g. engaging) the flange of the syringe plunger and a shaft reaching through an opening of a drive head housing (e.g. without bearing against an edge of the opening as set forth above) and also at least partially reaching through the pressure sensor support.

The drive head also may comprise means for generating a rotational movement (around an axis that is parallel to the direction of movement of the syringe plunger that will be generated by the drive head) and/or an axial movement (along the direction of the movement of the syringe plunger that will be generated by the drive head) of the holding element in order to move the holding element from an open position usable for arranging the syringe at the drive head into a closed position in which it holds the flange of the syringe plunger (after the syringe has been arranged at the drive head).

For example, the means comprise an actuating device for moving the holding element, the actuating device being configured to be manually operated from outside the housing, wherein the holding element can be moved from the closed position into the open position by moving the actuating device from a starting position to an open position, and wherein the actuating device is configured in such a way that it is decoupled from the holding element in the starting position.

More over, the means for generating a rotational and/or an axial movement can comprise resilient means that tend to hold the actuating device in the starting position, the starting position of the actuating device corresponding to the closed and backward position of the holding element. For example, the actuating device comprises a lever that is pre-tensioned by the resilient means. As the actuating device is decoupled from the holding element in the starting position it is avoided that parasitic forces are transmitted to the holding element via the drive head housing and the actuating device.

In particular, the means for generating a rotational and/or an axial movement of the holding element comprise a first interacting element connected to the actuating device and a second interacting element (directly or indirectly) connected to the holding element (e.g. to a shaft of the holding element) such that by operating the actuating device the first interacting element will be pushed against the second interacting element thereby pivoting the holding element towards the open position. Further, the means for generating a rotational and/or an axial movement can comprise a third interacting element connected to the actuating device (or formed by the actuating device) and a fourth interacting element connected to the holding element, wherein by operating the actuating device the third interacting element pushes against the fourth interacting element such that the holding element will be moved linearly. Thus, by operating the actuating means the holding element can be moved from a first position (closed and backward position) towards a second position (open and forward position).

Also, the means for generating a rotational and/or an axial movement may comprise resilient means that tend to hold the holding element in the closed and backward position.

According to another embodiment of the invention, the drive head comprises a latching mechanism that locks the holding element in the open and forward position. When the holding element is locked in that position the actuating device can be released wherein the actuating device will return in its starting position due to the return force of the resilient means. If the syringe plunger is pushed against the contact portion of the drive head, the holding element is released and will move into its closed and backward position (due to the pre-tensioning via the above mentioned resilient means). The resilient means exerting a return force on the actuating means will move the actuating means in a position in which the first and the third interacting elements (connected to the actuating device) are located with a distance from the second and fourth interacting elements (connected to the holding element) even if the holding element snapped back into its closed and backward position such that the holding element is decoupled from the actuating device.

It is noted that due to the pre-tensioning of the holding element a parasitic force on the contact portion of the drive head housing and thus on the pressure sensor will occur. However, the value of this parasitic force can be determined and taken into account.

In particular, the drive head comprises two rotatable holding elements such that the syringe plunger can be centered between the two holding elements. For example, the holding elements are rotatably coupled to one another such that if one of the holding elements is rotated, the rotational movement is transferred to the other holding element such that the holdings elements will perform a dependent rotation. For example, the rotational movement is transferred via gear wheel segments arranged at the first and the second holding element. However, this kind of coupling of the holding elements is known in principle from the prior art such that it will not be discussed in greater detail.

It is noted, however, that it is not necessary that the drive head comprises two rotatable holding elements. Rather, the drive head may have only one rotatable holding element, wherein the syringe plunger may be arranged between the rotatable holding element and a non-rotatable holding element (i.e. a holding element that cannot be rotated relative to the housing).

The invention also relates to a syringe pump comprising a drive head as described above.

The embodiments of the invention will be described in more detail hereinafter with reference to the drawings, in which:

FIGS. 7-11 show further views of the drive head.

Figure 1:
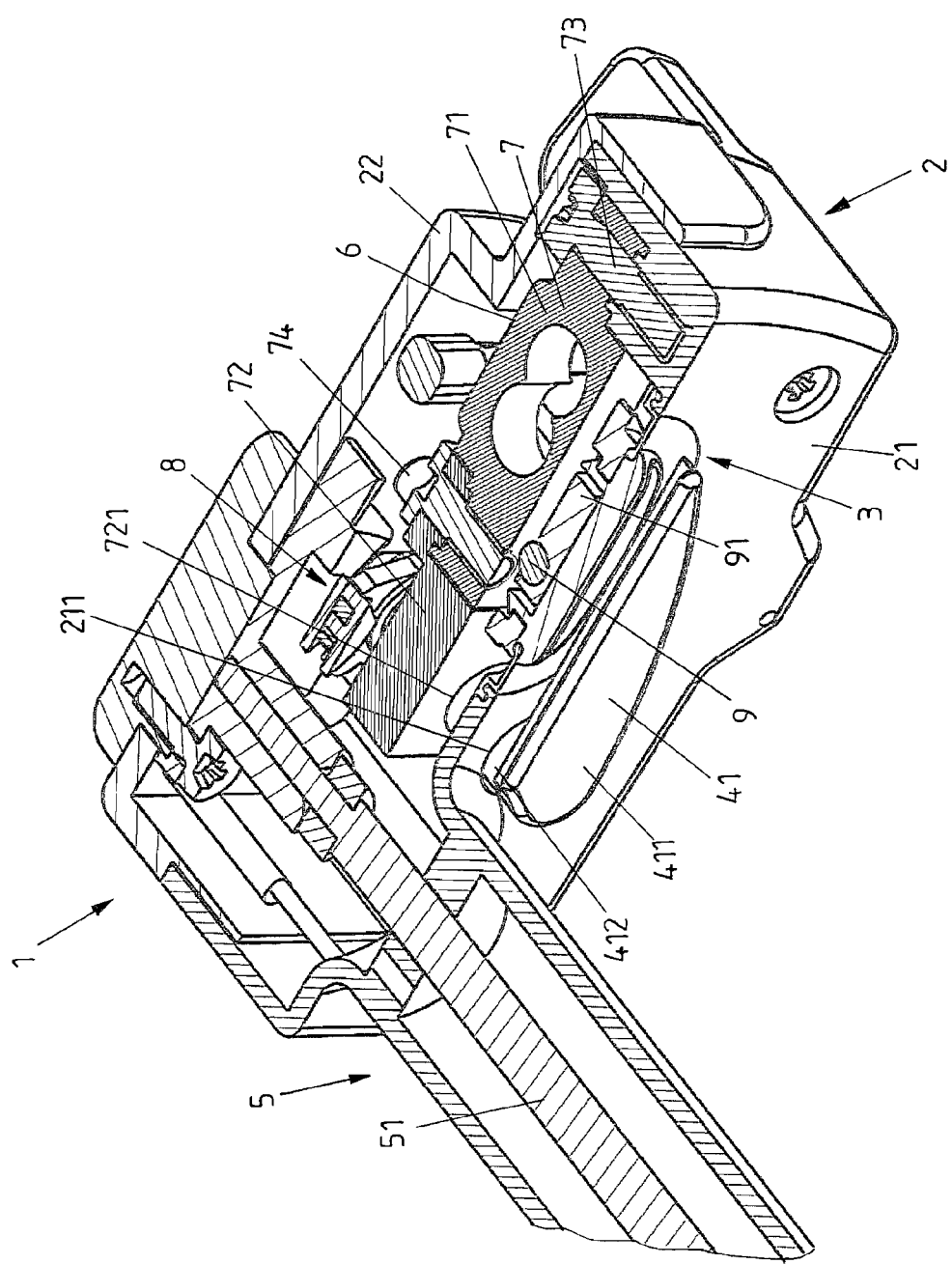
FIG. 1 illustrates a sectional view of a syringe pump drive head according to an embodiment of the invention.

The syringe pump drive head 1 according to the invention illustrated in FIG. 1 comprises a housing 2 consisting of a front part 21 that at least partially faces towards a syringe (not shown) when the drive head is in operation and a backward part 22.

Arranged in a front sidewall of the front housing part 21 is a contact portion 3 of the drive head. The contact portion 3 is configured to be pushed against the flange of a plunger of the syringe and to move the plunger relative to a barrel of the syringe in order to eject liquid from the syringe. During operation of the syringe pump the drive head is moved via a moving mechanism 5 comprising a screw drive mechanism generating a linear movement of the contact portion 3 along an axis 51 of the screw drive mechanism.

The drive head 1 further comprises two holding elements in form of rotatable anti-siphon arms 41, 42, wherein FIG. 1 shows a part of one of the arms, only. Both arms are shown for example in FIG. 4.

The arms 41, 42 are configured to engage a flange of the syringe plunger in order to prevent a siphon movement of the plunger, i.e. a movement away from the contact portion 3. For this, the arms 41, 42 each comprise a gripping element 411, 421 and a shaft 412, 422 connected to the gripping element 411, 421 such that the gripping elements 411, 421 can be rotated via the shaft 412, 422 between an open position in which the arms (i.e. the gripping elements) do not engage the flange of the syringe plunger and a closed position in which the arms engages the flange and, for example, hold the plunger flange in contact with the contact portion 3 of the drive head.

The drive head 1 further comprises a pressure sensor in form of a strain gauge 6 (not visible in FIG. 1) for determining an inner pressure in the syringe. The strain gauge 6 is attached to a pressure sensor support 7 arranged within the housing 2. The pressure sensor support 7, in turn, is arranged and configured in such a manner that a force exerted by the syringe plunger on the contact portion 3 is transferred via the pressure sensor support 7 to the strain gauge 6. That is, the force applied to the bearing section 3, and thus the inner pressure in the syringe, can be measured using an electrical signal generated by the strain gauge 6. Although a strain gauge is used as pressure sensor in this embodiment, other suitable pressure sensors could also be used.

The shafts 412, 422 of the anti-siphon arms 41, 42 are mounted via the pressure sensor support 7. In particular, the pressure sensor support 7 comprises a first part 71 to which the strain gauge 6 is attached and a second part in the form of an arm mount 72 via which the shafts 412, 422 are mounted. The first part 71 is connected to the arm mount 72 via a screw 75.

The shafts 412, 422 reach through openings 211, 212 in the front housing part 21 and through openings 721, 722 formed by the arm mount 72. Further, the shafts 412, 422 are connected to means for generating a rotational movement of the arms 41, 42 as will be explained in more detail further below.

Further more, the shafts 412, 422 are solely mounted via the arm mount 72, i.e. they reach through openings 211, 212 of the front housing part 21, but they do not lie against the inner edge of the openings 211, 212 during the operation of the drive head ("floatingly mounted" arms). Thus, it is avoided that movements of the arms 41, 42 are transferred to the contact portion towards the strain gauge 6 during drive head operation such that perturbations of the pressure sensor signal due to such arm movements are reduced or completely avoided.

Figure 2:
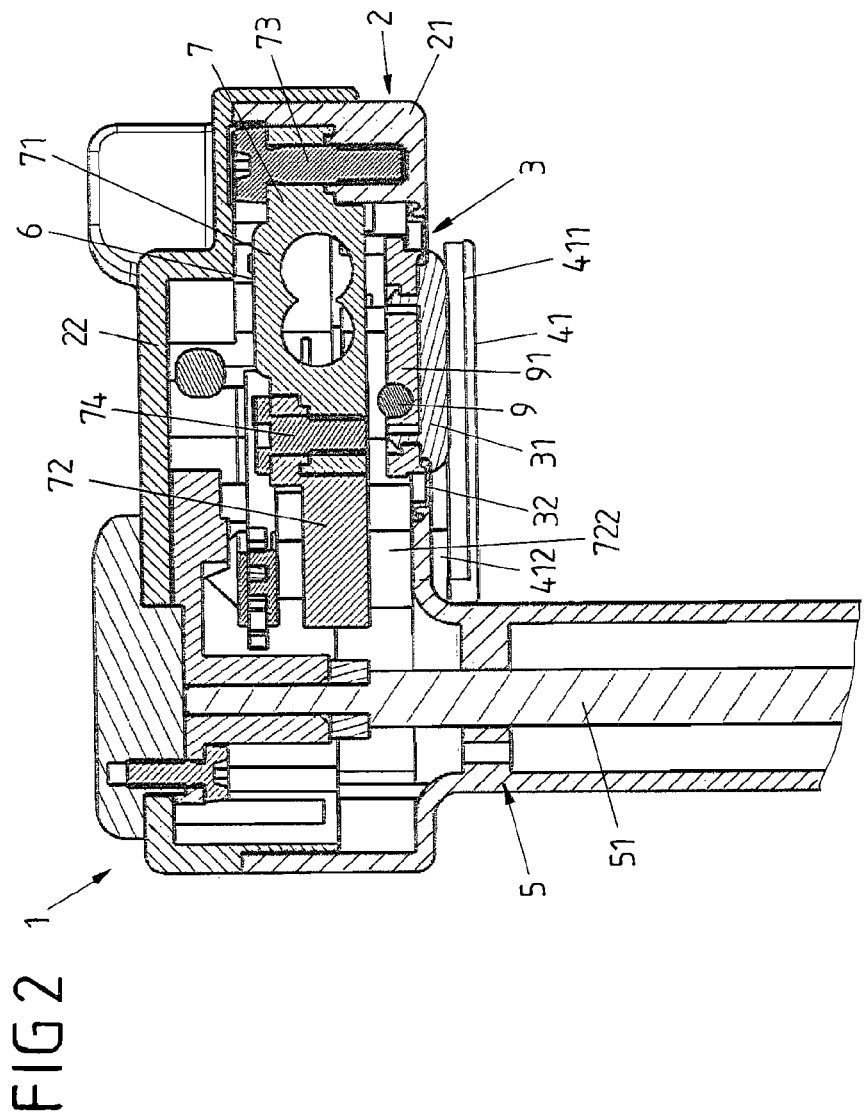
FIG. 2 illustrates a sectional view of the drive head according to FIG. 1 from another point of view.
Figure 3:
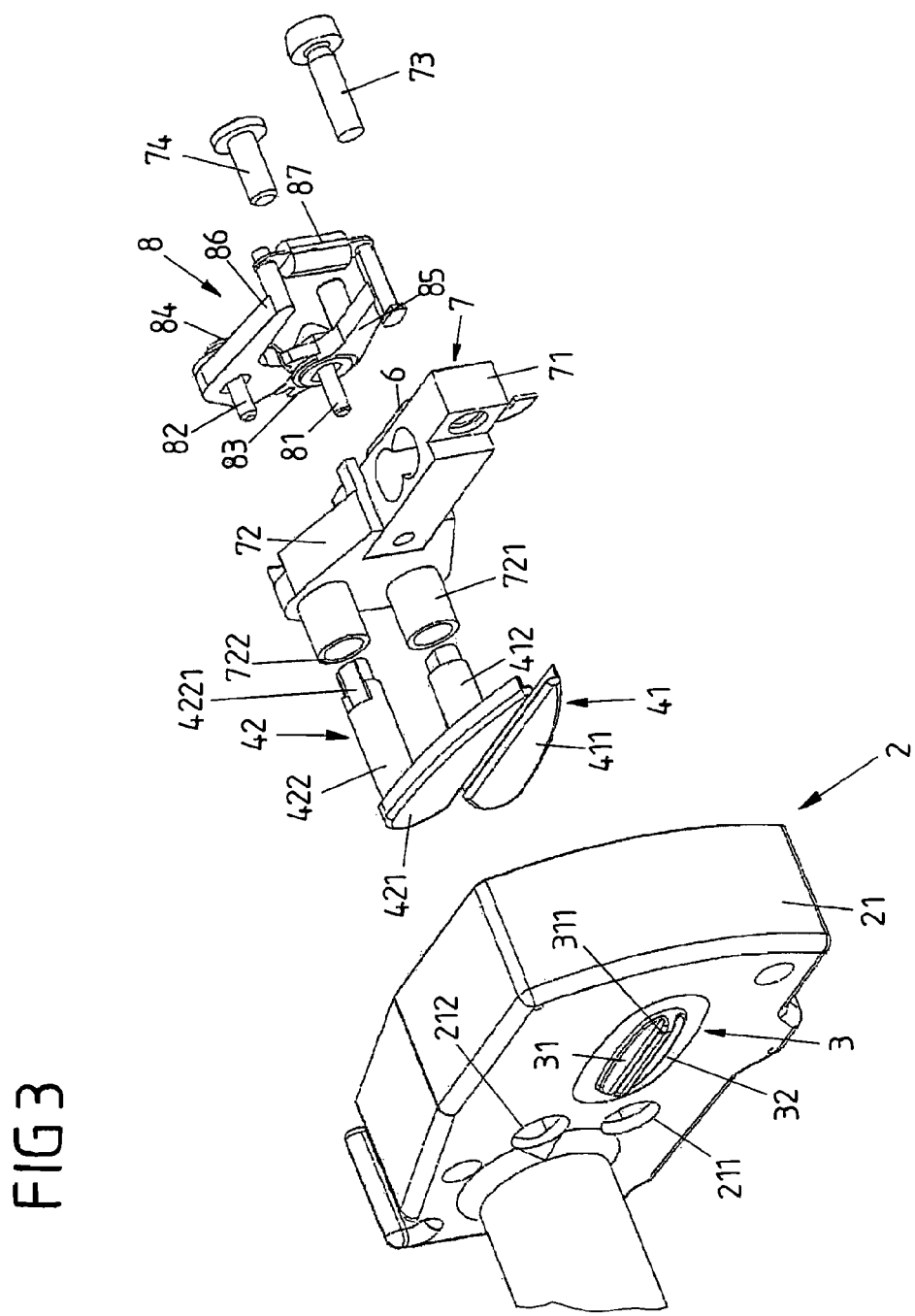
FIG. 3 illustrates an exploded view of components of the drive head of FIG. 1.

As best shown in FIGS. 2 and 3, the contact portion 3 comprises a contact element 31 to which the end face of the syringe plunger flange will bear when the drive head is in operation. The contact element 31 comprises (as shown in FIG. 3) an oval basic section and a longitudinal protrusion 311 protruding from the basic section (and thus, from the front housing part 21) which will be in mechanical contact with the plunger flange end face.

The contact element 31 is mounted to the front part 21 of the housing 2 via a flexible (and elastic) element in form of a ring-shaped membrane 32. The membrane 32 on the one hand is connected (e.g. adhesively bonded) to the contact element 31 and on the other hand to the front housing part 21, wherein the connection of the membrane 32 to the contact element 31 and the housing part 21 may be a sealed connection. Also, the material of the membrane and its thickness may be chosen in such a way that a movement of the contact portion 31 will be transferred towards the pressure sensor support 7 and thus towards the strain gauge 6 as accurate as possible.

As also shown in FIG. 2, the pressure sensor support 7 is connected to the housing 2 (i.e. the front housing part 21) via a single connection point, only, wherein the connection point is realized by a screw 73. It is noted that instead of a screw other means for realizing the single connection point are conceivable, for example, a latching connection or adhesive bonding. By providing a single connection point only, the housing and the pressure sensor are separated as much as possible in order to avoid that deformations of the housing are transmitted to the pressure sensor.

Further more, the drive head 1 comprises a pressure transmitting element in form of a spherical element 9, which is arranged in a carrier plate 91. The carrier plate 91 and thus the spherical element 9 will be moved when the syringe plunger presses against the contact portion 3 such that a section of the spherical element 9 will be pushed against the first part 71 of the sensor support 7. Therefore, a force exerted on the contact portion 3 will be transferred via the plate 91, the spherical elements 9 and the support part 71 towards the strain gauge 6. It is possible that the carrier plate 91 is pivotably mounted to the housing 2 such that if the bearing section 3 is moved (deflected) the carrier plate 91 will perform a pivot movement towards the pressure sensor support 7, thereby pushing the spherical element 9 against the pressure sensor support 7.

FIG. 3 shows an exploded and perspective view of some of the components of the drive head 1 of FIGS. 1 and 2. Although the arms 41, 42 are shown on an interior side of the front housing part 21 in FIG. 3, it is obvious that in the assembled state of the drive head, the gripping elements 411, 421 will be located outside the front housing part 21 and the shafts 412, 421 will extend through the openings 211, 212 of the housing part 21.

The shafts 412, 422 of the arms 41, 42 are mounted in openings 721, 722 of the arm mount 72 of the pressure sensor support 7. A portion of the openings 721, 722 is formed by hollow cylindrical parts protruding from a basic portion of the arm mount 72, the shafts 412, 422 reaching through the hollow cylindrical parts towards means 8 for generating a rotational and axial movement of the arms 41, 42. The means 8 comprise axles 81, 82 that are connected to the shafts 412, 422 and may also partially reach through the arm mount 72.

Further, the axles 81, 82 are coupled to gear wheel segments 83, 84 such that a rotatable connection is established between the axles 81, 82. Further, connecting arms 85, 86 extend from the axles 81, 82, wherein the free ends of the connecting arms 85, 86 are connected to a spring 87 biasing the connecting arms 85, 86 in such a way that the anti-siphon arms 41, 42 tend to remain in their closed position. The principle of the means 8 will be explained in more detail with respect to FIGS. 4 to 6.

Figure 4:
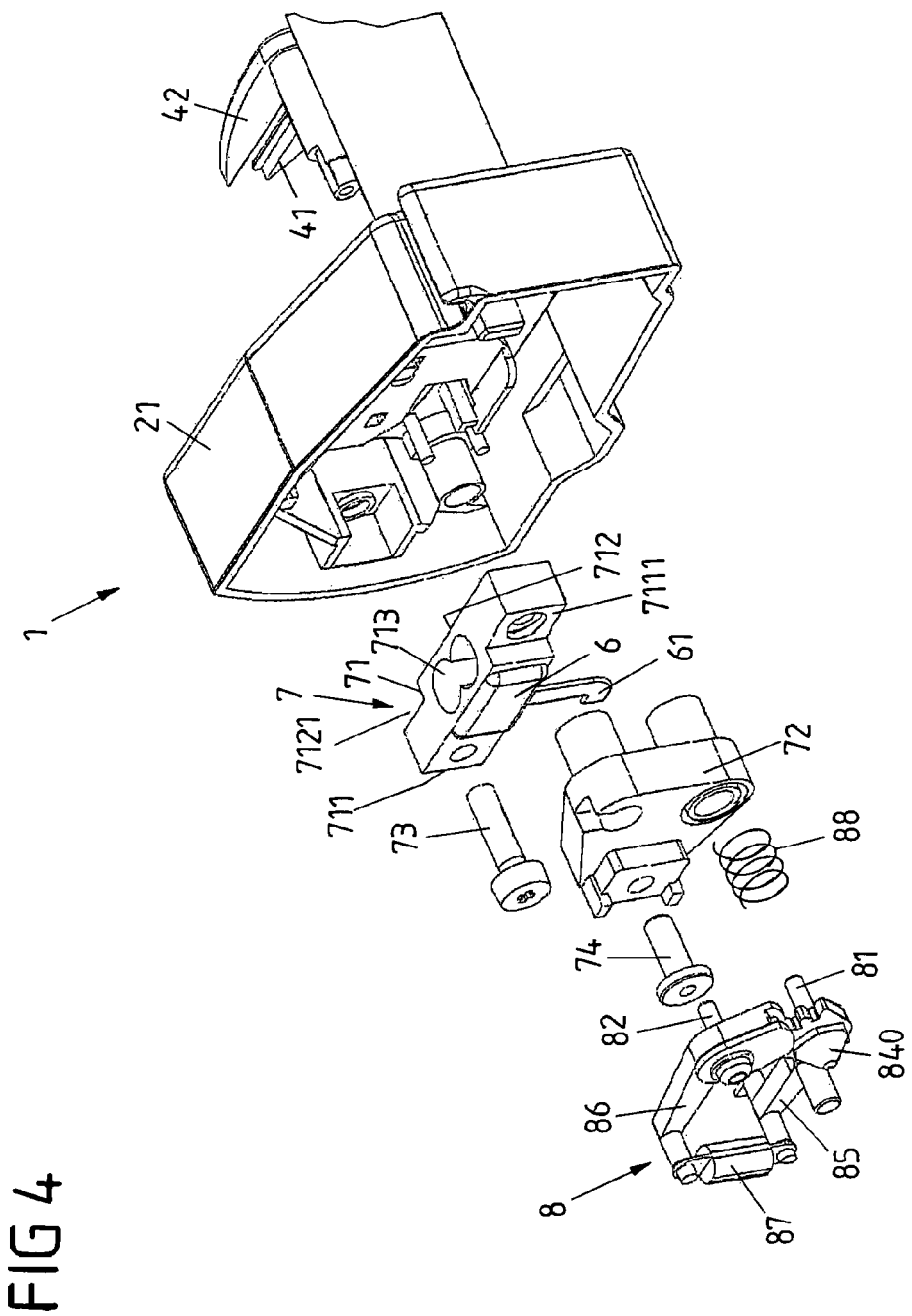
FIG. 4 is another illustration of the components of FIG. 3.

FIG. 4 shows the components illustrated in FIG. 3 in another perspective, wherein the strain gauge 6 can be seen to be connected to a backward surface 711 of the first part 71 of the sensor support 7. Further shown is a cable 61 connecting the strain gauge 6, for example, to a voltage supply and/or means for evaluating a sensor signal (not shown). The backward surface 711 runs parallel to a front surface 712 of the first support part 71. Both the backward and the front surface 711, 712 comprise a notch 7111, 7121 to provide a connecting portion through which the screws 73 and 74 extend in order to connect the sensor support 7 to the housing 2 and to connect the arm mount 72 to the first sensor support part 71, respectively.

Further more, the first support part 71 comprises a through opening 713 running essentially parallel to the backward and the front surface 711, 712. The through opening 713 has a cross section (along a plane that extends perpendicular with respect to the backward and the front surface 711, 712) that is composed of two overlapping circles, wherein the circle centres are positioned along a line running parallel to the backward and the front surface 711, 712. It is due to this design of the through opening 713 that if the front surface 712 is deformed under a load applied via the bearing section 3, the backward surface 711 deforms in a similar way such that the backward and the front surface 711, 712 still run parallel to one another even is the support part 71 is deformed.

In particular, the sections of backward and the front surface 711, 712 located on a side of the through opening 713 that faces towards the arm mount 72 and on a side that faces away from the arm mount 72, respectively, will still run parallel to one another and parallel to the plane in which the backward and the front surface 711, 712 originally extended (before a deformation of the support part 71) even if a force is applied to the front surface 711. This has the effect that the arm mount 72, which is connected to a section of the support part 71 located laterally to the through opening 713, will not be inclined if the sensor support part 71 deforms. Rather, it might only be displaced along the direction of movement of the drive head such that the arms 41, 42 may only be shifted along the syringe axis but will not (or at least only slightly) incline with respect to the syringe plunger flange.

Moreover, the means 8 for generating a rotational and axial movement not only generate a rotational movement of the arms 41, 42 but also a linear movement in order to be able to move the arms a certain distant away from the front housing part 21 when the syringe is arranged on the drive head. As shown in FIG. 4 another spring 88 is provided between the arm mount 72 and the lower connecting arm 85, the spring 88 tending to hold the arms in a backward position. Thus, the spring 88 will exert a reset force on the lower connecting arm 85 (and as this arm is connected to the upper connecting arm 86 also on the upper connecting arm) such that the anti-siphon arms 41, 42 will tend to return towards their backward position where they hold the syringe plunger in contact with the contact portion 3.

Figure 5:
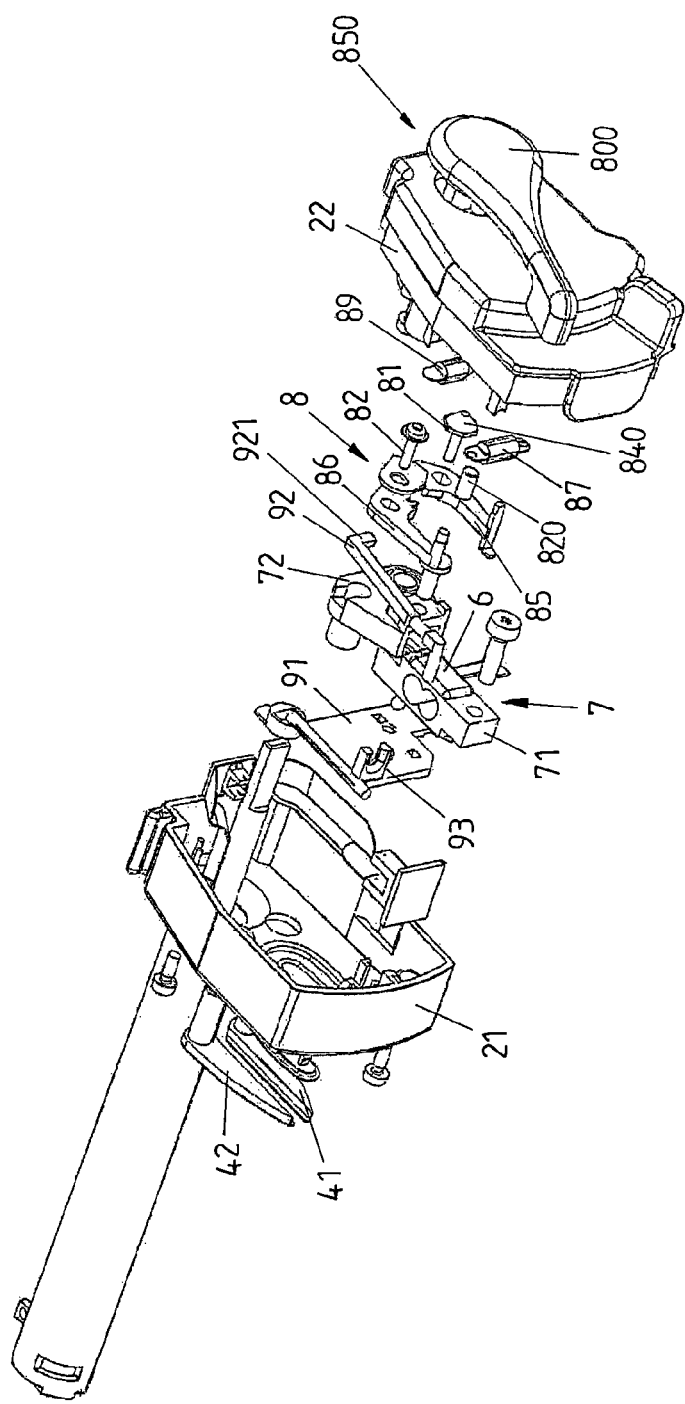
FIG. 5 illustrates another exploded view of the drive head of FIG. 1.
Figure 6:
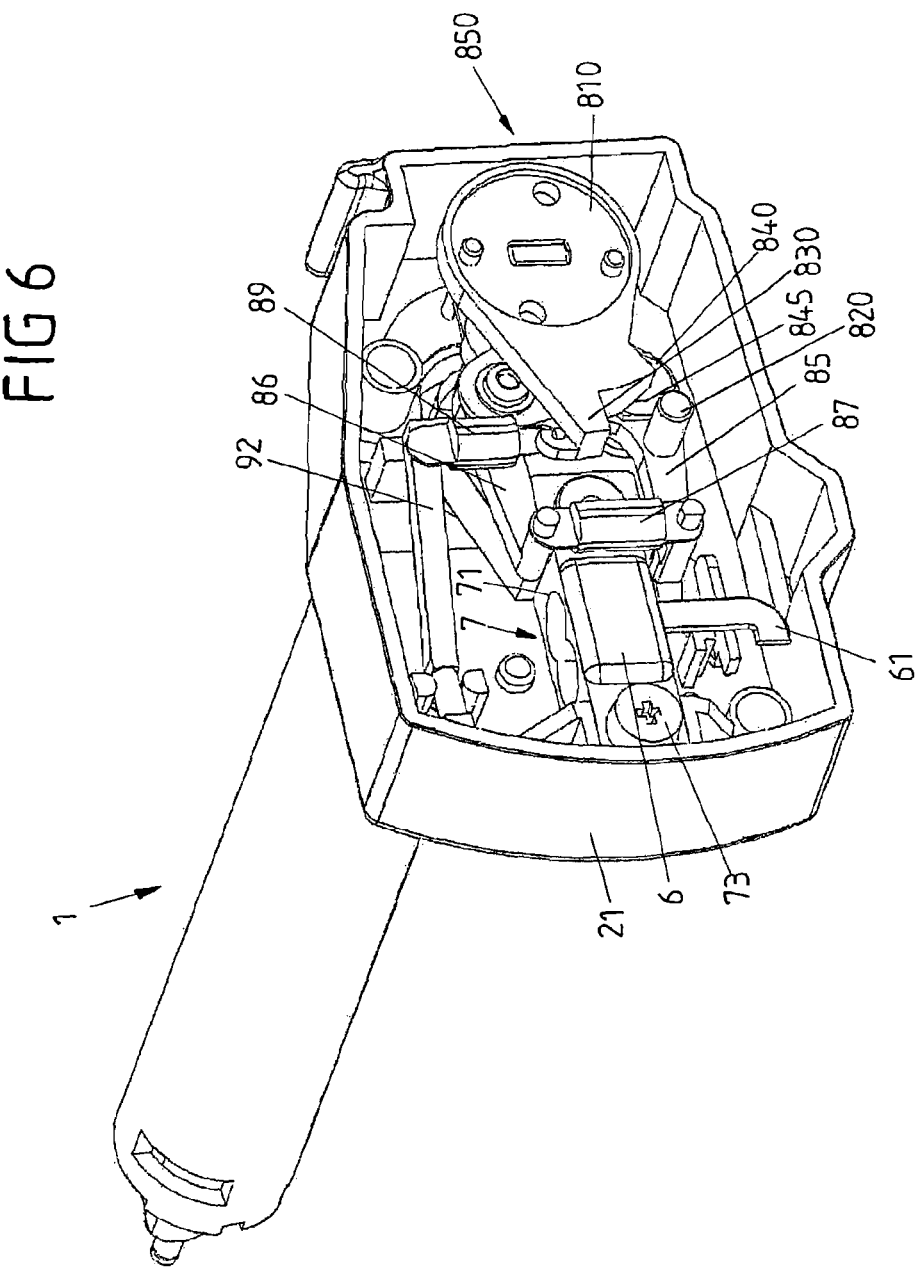
FIG. 6 is a perspective view of the interior of the drive head according to FIGS. 1 to 5.

FIGS. 5 and 6 illustrate the components of the means 8 for generating a rotational and axial movement of the anti-siphon arms 41, 42 in more detail.

The means 8 comprise an actuating device 850 including a lever 800 that is arranged outside the housing 2. The lever 800 is connected through a side wall of the housing to a transmission component 810 located in the interior of the housing 2. Thus, a rotation of the lever 800 will cause the transmission component 810 to rotate, too (i.e. the transmission component 810 will follow the rotation of the lever).

Further more, the means 8 comprise a first interacting element in the form of a projection 830 of the transmission component 810 (i.e. the projection 830 is integrally connected to the actuating device 850) and a second interacting element in the form of a cylindrical protrusion 820 connected to the lower connecting arm 85 (thus the protrusion 820 is indirectly connected to the anti-siphon arms 41, 42 via the connection between the connecting arms 85, 86 and the arms 41, 42).

If the lever 800 is rotated from a starting position in anti-clockwise direction the projection 830 will be pushed against the protrusion 820 such that the lower connecting arm 85 and the upper connecting arm 86 will be rotated against the biasing force of spring 87. Due to the rotation of the connecting arm the anti-siphon arms 41, 42 will be rotated also such that by rotating the lever 800 in anti-clockwise direction the arms 41, 42 can be rotated from a closed position into an open position, in which the distance between the arms is larger than in the closed position.

The actuating mechanism 850 further comprises a further (third) interacting element in the form of a tapered end 840 of the lower axis 81. Assigned to the tapered end 840 is a fourth interacting element in the form of an interacting portion 845 of the transmission component 810, wherein the interacting portion 845 will push against the tapered end 840 if the lever is pivoted in anti-clockwise direction such that the lower axis 81 and the connected upper axis 82 will be moved axially (along the direction of movement of the drive head) from a backward position towards a forward position.

Following the linear movement of the axles 81, 82 the anti-siphon arms 41, 42 will move axially also, i.e. away from the contact portion 3 into the forward position. Thus, by rotating the lever 800 the anti-siphon arms 41, 42 can be moved radially and axially from a first position (closed arms, backward position with respect to the contact portion 3) into a second position (open arms, forward position with respect to the contact portion 3). A "forward position" of the arms means that their distance from the contact portion 3 (i.e. from the housing 2) is larger than in the "backward position".

The drive head 1 further comprises a latching mechanism that locks the arms 41, 42 after they have been moved in the open and forward position by rotating the lever 800. The latching mechanism comprises an engagement element 92, wherein after a rotation of the lever 800 in the open and forward position a projection 921 of the engagement element 92 engages a groove 4221 (FIG. 3) provided in the shaft 422 of the upper arm 42 in such a way that the arms 41, 42 are locked in the open and forward position. Also, as the lever 800 is biased via spring 89, it will return in its starting position if the arms 41, 42 are locked in the open position. In the starting position of the lever 800 the projection 830 and the interacting portion 845 are not any more in contact with the protrusion 820 and the tapered ending 840, respectively, such that the arms 41, 42 are decoupled from the transmission component 810 and the lever 800.

The engagement element 92 is held in a section 93 of the plate carrier 91, wherein carrier plate will be moved away from the housing 2 if the syringe plunger pushes against the contact element 31. Thus the engagement element is moved also and released from its locked position such that the arms 41, 42 are not locked anymore. If the syringe is removed from the drive head, the contact element will return to its outward position again due to the elasticity of the surrounding membrane 32. A spring may be used instead or in addition to a membrane.

It is noted, however, that the described latching mechanism is only optional. It is also possible that the arms 41, 42 are held in the open position manually, i.e. by holding the lever 800 in its "open" position during the arrangement of the syringe at the drive head. After the syringe is arranged the lever 800 is releases such that the arms 41, 42 snap back into the closed and backward position.

Figure 7:
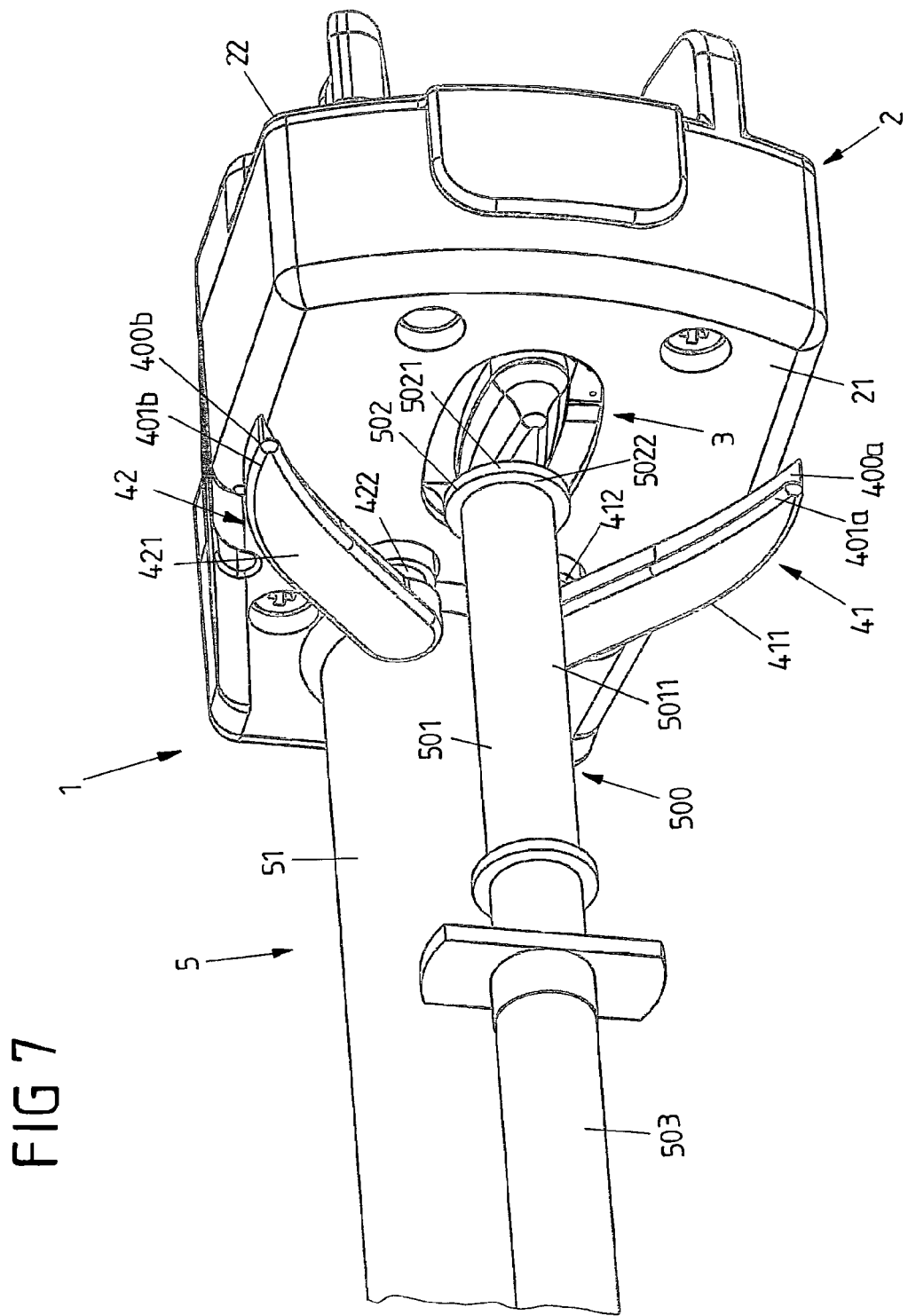
Figure 8:
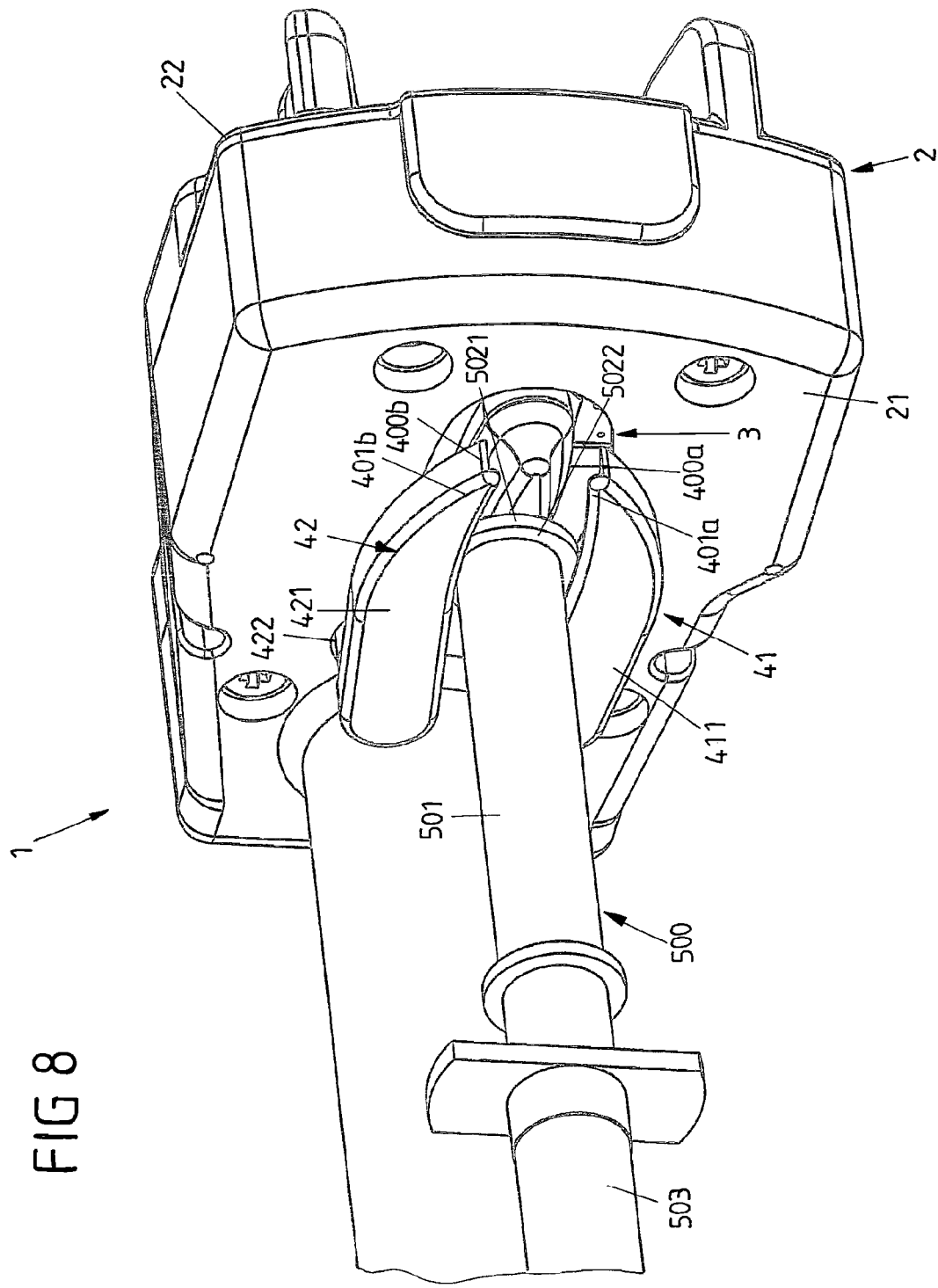

FIGS. 7 and 8 depict further views of the drive head 1, wherein a syringe 500 is shown to be arranged at the drive head, the syringe 500 comprising a plunger 501. A typical syringe plunger as shown in FIG. 7 comprises a main portion 5011 and a flange 502 arranged at an end of the main portion, the flange protruding from the main portion, i.e. the flange 502 has a larger diameter than the plunger main portion 5011.

The syringe is arranged at the drive head in such a way that an end face of the flange 502 of the syringe plunger 501 bears against the contact portion 3 of the drive head such that when the contact portion 3 is moved, the plunger 501 will be moved within a barrel 503 of the syringe 500 such that liquid will be ejected from the syringe.

As set forth above, the drive head comprises means 8 for generating a rotational and axial movement of the anti-siphon arms 41, 42 in order to move the arms from an open and forward position ("second position", FIG. 7) into a closed and backward position ("first position", FIG. 8). After the arrangement of the syringe at the drive head the arms 41, 42 will snap back into the first position, i.e. into the closed and backward position, in such a way that the gripping elements 411, 421 bear against a peripheral edge 5021 of the flange 502.

More over, the gripping elements 411, 421 each comprise a first section 400a, 400b and a second section 401a, 401b protruding beyond the first section, wherein in the closed and backward position of the arms 41, 42 only the first sections 400a, 400b of the gripping elements 411, 421 bear against the peripheral edge 5021 of the flange 502, whereas the second sections 401a, 401b do not bear against the peripheral edge 5021 but lie against a front surface (front side) 5022 of the flange 502 that faces away from the contact portion 3.

It is noted, however, that it is also possible that the second sections 401a, 401b do not lie against the flange front surface 5022 in the closed and backward position of the arms 41, 42. In that case the second sections 401a, 401b are positioned in a distance from the front surface 5022 but are still positioned in such a way that they can block a siphon movement of the arms 41, 42, i.e. they still "engage" the plunger flange.

Figure 9B:
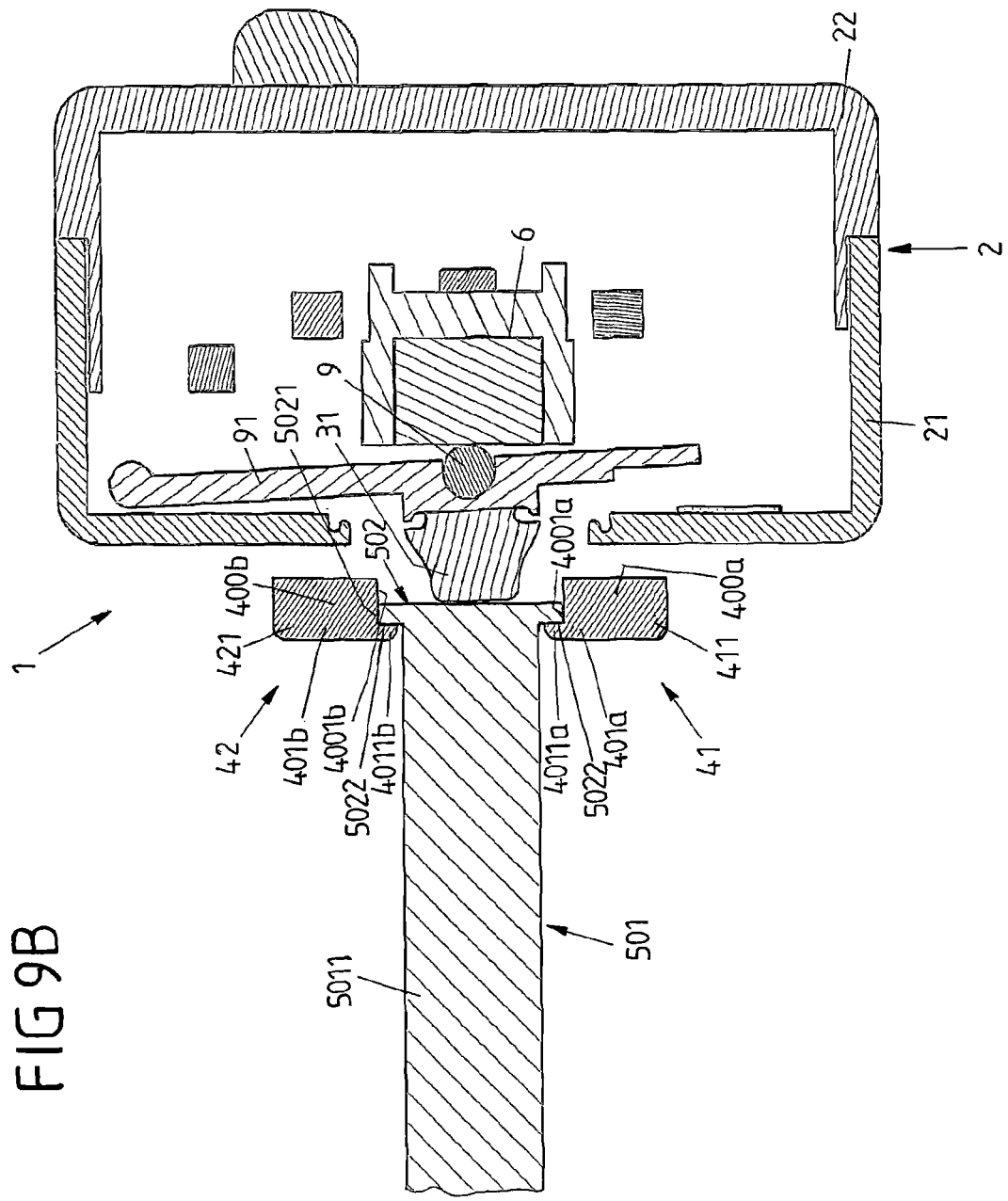

FIGS. 9A and 96 show sectional views of the drive head 1, wherein according to FIG. 9A the arms 41, 42 are in their closed positions but do not have yet reached the most backward position. After the arms 41, 42 were rotated by the means 8 (i.e. via the return force of the springs 87-89) until they bear against the peripheral edge 5021 of the flange 502 (as shown in FIG. 9A), the backward movement of the arms starts or continues (also by means of the return force of the springs 87-89) until the arms 41, 42 bear against the inner surface 5022 of the flange 502 as shown in FIG. 96.

In that example, the rotational movement and the axial movement are at least partially carried out successively. In order to generate this sequential movement the spring 87 (generating the rotational movement of the arms towards the closed position) and the spring 88 (generating the linear movement of the arms towards the backward position) are adapted accordingly. For example, the spring 87 comprises a higher spring constant than spring 88.

It is noted, however, that it is also possible that the rotational and the axial movement of the arms (from the second into the first position) is carried out simultaneously (or at least essentially simultaneously).

It is further noted that in the forward position the distance of the arms 41, 42 from the contact portion 3 is smaller than the thickness of the plunger flange 502 such that even if the arms are rotated in the closed position before being moved in the backward position it is avoided that the arms pass the flange 502. Thus, it is ensured that the arms in the closed position will bear against the peripheral edge 5021 of the flange 502.

The second sections 401a, 401b of the gripping elements 411, 421 extend beyond the first sections 400a, 400b such that "fingers" 4011a, 4011b protrude beyond an inner surface 4001a, 4001b of the first sections 400a, 400b. The length of the fingers 4011a, 4011b is smaller than the height of the plunger flange 502 such that inner surfaces 4001a, 4001b of the first sections 400a, 400b of the gripping elements bear against the peripheral edge surface 5021 of the flange 502 while the second sections 401a, 401b are not in contact with a main portion 5011 of the plunger.

As the fingers 4011a, 4011b are arranged perpendicular to the inner surfaces 4001a, 4001b of the first sections 400a, 400b an edge is formed between the first and the second sections, wherein the edge—viewed perpendicular to the plunger axis—extends essentially along the whole length of the gripping elements 411, 421. Further, the fingers 4011a, 4011b are slightly tapered towards the plunger 501, the tapering being realized by a bending of a front side portion of the fingers 4011a, 4011b.

Figure 10:
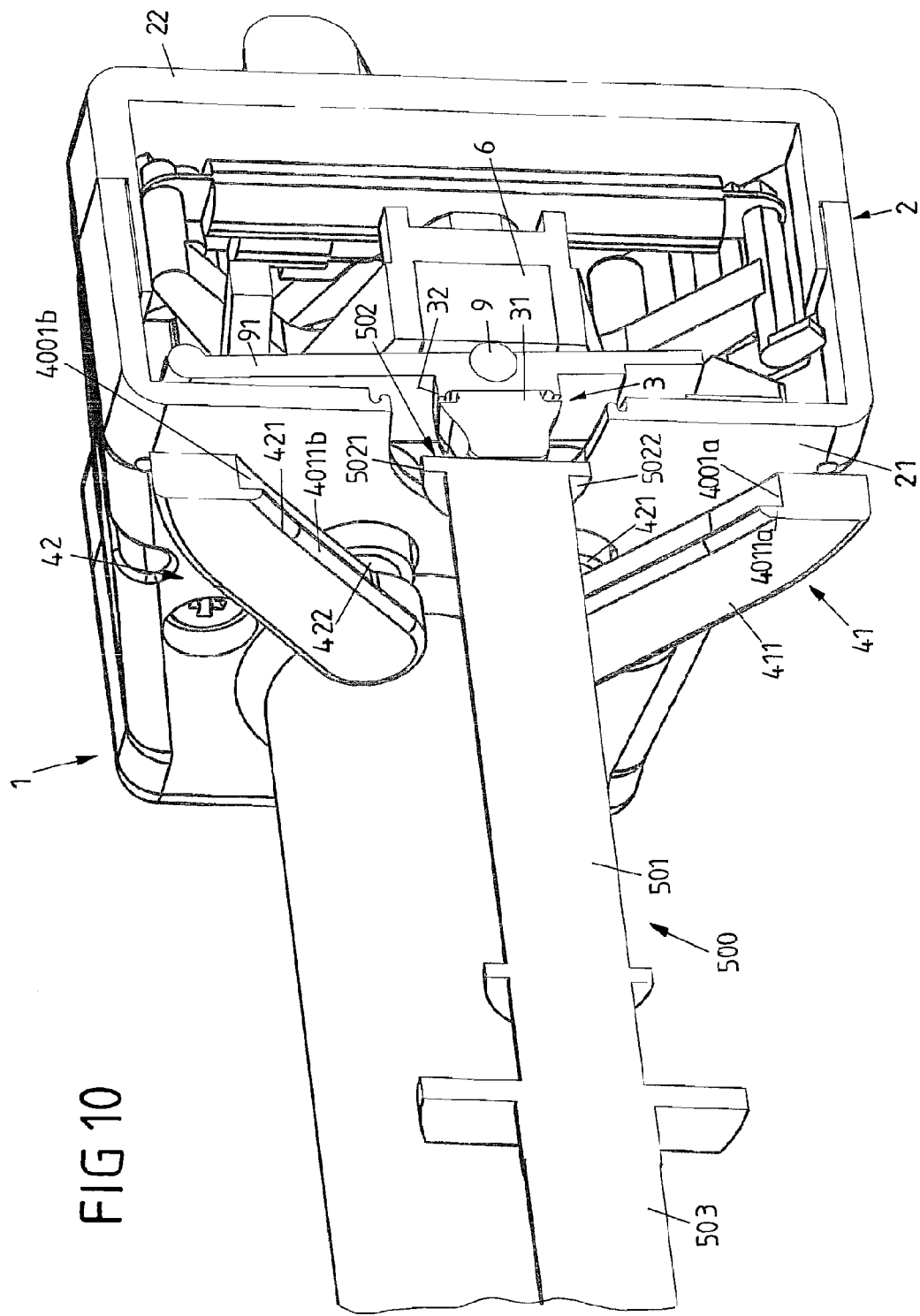

FIG. 10 (related to the open position of the arms 41, 42) and 11 (closed position) provide perspective views corresponding to FIGS. 7 and 8, respectively, wherein according to FIG. 11 the arms are in their closed but not yet in their most rearward position. It can be seen that the carrier plate 91 arranged between the finger 31 of the bearing portion 3 and the pressure sensor 6 may be mounted to a hinge portion of the housing such that a force applied to the finger 31 causes the support plate 91 to rotate such that the spherical element 9 is pushed against the pressure sensor device 6 by a rotational movement of the support plate 91.

It is noted that the principle of the means 8 described with respect to FIGS. 7 to 9 (moving the arms so as to bear against a peripheral edge of the flange in the first position) can be used with any kind of a syringe pump drive head. In particular, the principle of letting the arms 41, 42 bear against a peripheral edge of the flange can be used independently from the concept of floatingly mounting the arms 41, 42 as described with respect to FIGS. 1 to 6, i.e. the principle of letting the arms 41, 42 bear against a peripheral edge of the flange can be used also in connection with holding elements that are conventionally mounted, e.g. via the drive head housing.

REFERENCE SIGNS 1 drive head
2 housing
3 contact portion
5 moving mechanism
6 strain gauge
7 pressure sensor support
8 means for generating rotational and axial movement
9 spherical element
21 front part
22 back part
31 contact portion
32 membrane
41 first arm
42 second arm
51 axis
61 cable
71 first part
72 arm mount
73, 74 screw
81, 82 axis
83, 84 gear wheel segment
85, 86 arm
87, 88, 89 spring
91 carrier plate
92 engagement element
93 latching structure
211, 212 through opening
311 protrusion
400a, 400b first section
401a, 401b second section
411, 421 gripping element
412, 422 shaft
500 syringe
501 plunger
502 flange
503 barrel
711 backward surface
712 front surface
713 through opening
721, 722 opening
800 lever
810 transmission component
820 protrusion
830 projection
840 tapered end
845 interacting portion
850 actuating device
4001a, 4001b inner surface
4011a, 4011b finger
4221 groove
5011 main portion
5021 peripheral edge
5022 front surface
7111, 7121 notch

The invention claimed is:

1. A drive head for a syringe pump, comprising:
a housing;
a pressure sensor support connected to the housing;
a pressure sensor connected to the pressure sensor support;
a holding element connected to the pressure sensor support, the holding element extending through an opening in the housing and configured for holding a flange of a syringe plunger;
a rotational and axial movement mechanism connected to the holding element and including a protrusion; and
an actuating device connected to the housing and including a projection;
wherein the actuating device is movable into a first position with the projection of the actuating device in contact with the protrusion of the rotational and axial movement mechanism such that the holding element is rotated to an open position, and a second position with the projection of the actuating device being out of contact with the protrusion of the rotational and axial movement mechanism such that force transfer between the housing and the rotational and axial movement mechanism via the projection of the actuating device is prevented and the holding element is rotated to a closed position.

2. The drive head according to claim 1, further comprising a contact portion, wherein the pressure sensor support is arranged on a side of the contact portion that faces away from a syringe when the drive head is in operation.

3. The drive head according to claim 2, wherein the contact portion is arranged in a section of the housing.

4. The drive head according to claim 3, wherein the contact portion comprises a contact element arranged in such a manner that, when the drive head is in operation, the syringe plunger bears against the contact element, the contact element being mounted to the housing via a flexible element.

5. The drive head according to claim 2, wherein the pressure sensor support is arranged such that a force exerted by the syringe plunger on the contact portion is transferred to the pressure sensor through the pressure sensor support.

6. The drive head according to claim 2, wherein the pressure sensor comprises at least one strain gauge arranged at a side of the pressure sensor support that faces away from the contact portion.

7. The drive head according to claim 1, wherein the holding element is rotatably mounted at the pressure sensor support.

8. The drive head according to claim 1, wherein the holding element comprises a shaft that at least partially reaches through the pressure sensor support.

9. The drive head according to claim 1, wherein the actuating device comprises a spring that biases the actuating device toward a starting position.

10. The drive head according to claim 1, wherein the pressure sensor support comprises a first and a second part, the second part being connected to the first part via connecting means, wherein the pressure sensor is arranged at the first part and the holding element is mounted via the second part.

11. The drive head of claim 1 wherein a coupling between the pressure sensor support and the housing at an internal connection is the sole coupling point between the pressure sensor support and the housing.

12. The drive head of claim 1 wherein the actuating device includes a lever connected to a transmission component, the transmission component including the projection.

13. The drive head of claim 1 wherein the housing includes an opening through which a shaft of the holding element extends, wherein no part of the shaft of the holding element makes contact with the housing.

14. The drive head of claim 1 wherein a first axial position of the holding element with the actuating device in the first position is different from a second axial position of the holding element with the actuating device in the second position.

* * * * *